(12) United States Patent
Sarmientos et al.

(10) Patent No.: US 7,070,958 B2
(45) Date of Patent: Jul. 4, 2006

(54) METHODS OF MAKING PRO-UROKINASE MUTANTS

(75) Inventors: Paolo Sarmientos, Lecco (IT); Massimiliano Pagani, Castelli Calepio (IT)

(73) Assignee: Thrombolytic Science, Inc., Boston, MA (US)

( * ) Notice: Subject to any disclaimer, the term of this patent is extended or adjusted under 35 U.S.C. 154(b) by 88 days.

(21) Appl. No.: 10/826,598

(22) Filed: Apr. 16, 2004

(65) Prior Publication Data

US 2005/0019863 A1    Jan. 27, 2005

Related U.S. Application Data

(60) Provisional application No. 60/463,930, filed on Apr. 18, 2003, provisional application No. 60/464,003, filed on Apr. 18, 2003.

(51) Int. Cl.
*C12P 21/06* (2006.01)

(52) U.S. Cl. ............... 435/69.1; 435/6; 435/320.1; 435/252.1; 530/350; 530/300; 424/94.63; 424/94.64; 604/509; 604/194

(58) Field of Classification Search ............ 435/69.1, 435/6, 320.1, 252.1; 530/350, 300; 424/94.63, 424/94.64; 604/509, 194
See application file for complete search history.

(56) References Cited

U.S. PATENT DOCUMENTS

| | | | |
|---|---|---|---|
| 5,472,692 A | 12/1995 | Liu et al. | 424/94.63 |
| 5,626,841 A | 5/1997 | Gurewich | 424/94.63 |
| 5,759,542 A | 6/1998 | Gurewich | 424/94.64 |
| 5,866,358 A | 2/1999 | Brandazza et al. | 435/69.1 |
| 6,364,893 B1 | 4/2002 | Sahatjian et al. | 606/194 |
| 6,409,716 B1 | 6/2002 | Sahatjian et al. | 604/509 |

OTHER PUBLICATIONS

Orsini et al., Eur. J. Biochem, vol. 195, pp. 691-697.*
Yuming et al., Chinese Journal of Biotechnology, vol. 13(4), pp. 233-238, 1997.*
Ning et al., Circulation Research, vol. 90 (7), pp. 757-763, 2002.*
Gurewich et al., "Effective and Fibrin-specific Clot Lysis by a Zymogen Precursor Form of Urokinase (Pro-urokinase)", J. Clin. Invest., vol. 73, pp. 1731-1739 (1984).
Heckel et al., "Prediction of the three-dimensional structure of the enzymatic domain of t-PA", J. Comp. Aided Mol. Des., vol. 2, pp. 7-14 (1988).
Liu et al., "Inactivation of the Intrinsic Activity of Pro-urokinase by Diisoprophyl Fluorophosphate Is Reversible", The Journal of Biological Chemistry, vol. 270(15), pp. 8408-8410 (1995).
Liu et al., "A comparative Study of the Promotion of Tissue Plasminogen Activator and Pro-Urokinase-induced Plasminogen Activation by Fragments D and E-2 of Fibrin", J. Clin. Invest., vol. 88, pp 2012-2017 (1991).
Liu et al., "Fragment E-2 from Fibrin Substantially Enhances Pro-urokinase-Induced Glu-Plasminogen Activation. A Kinetic Study Using the Plasmin-Resistant Mutant Pro-urokinase Ala-158-rpro-UK", Biochemistry, vol. 31, pp. 6311-6317 (1992).
Liu et al., Prourokinase Mutant That Induces Highly Effective Cost Lysis Without Interfering With Hemostatsis, Circulation Research, vol. 90, pp. 757-763 (2002).
Liu et al., "A Site-Directed Mutagenesis of Pro-Urokinase at the Flexibir Loop Region of Active Domain", Advances in Gene Technology: Protein Engineering and Beyond, (Abstract Only).
Nienaber et al., "Conformational Similarities between One-chain and Two-Chain Tissue Plasminogen Activator (t-PA): Implications to the Activation Mechanism on One-Chain t-PA", Biochemistry, vol. 31, pp. 3852-3861 (1992).
Orsini et al., "Efficient renaturation and fibrinolytic properties of prourokinase and a deletion mutant expressed in *Escherichia coli* as inclusion bodies", Eur. J. Biochem., vol. 195, pp. 691-697 (1991).
Pannell et al., "Activation of Plasminogen by Single-Chain Urokinase or by Two-chain Urokinase—A Demonstration That Single-Chain Urokinase Has a Low Catalytic Activity (Pro-Urokinase)", Blood, vol. 69(1), pp. 22-26 (1987).
Peterson et al., "Quenching of the Amidolytic Activity of One-Chain Tissue-Type Plasminogen Activator by Mutation of Lysine-416", Biochem., vol. 29, pp. 3451-3457 (1990).
Verde et al., "Identification and primary sequence of an unspliced human urokinase poly(A)+ RNA", Proc. Natl. Acad. Sci., vol. 81, pp. 4727-4731 (1984).

* cited by examiner

*Primary Examiner*—Kathleen M. Kerr
*Assistant Examiner*—Hope Robinson
(74) *Attorney, Agent, or Firm*—Fish & Richardson P.C.

(57) ABSTRACT

Methods are provided for producing non-glycosylated, single-chain and two-chain pro-urokinase (pro-UK) mutants. The methods include cultivating a specific *E. coli* type B strain that has been transformed with specific plasmids carrying a cDNA sequence that encodes pro-UK mutants and carries specific promoter sequences. Products produced by the methods have medical use for thrombolysis performed while sparing hemostatic clots, e.g., for particular applications such as after a stroke or heart attack.

24 Claims, 4 Drawing Sheets

Construction of pET29-uPA(M5) expression plasmid

METHODS OF MAKING PRO-UROKINASE MUTANTS

CROSS-REFERENCE TO RELATED APPLICATIONS

This application claims priority from U.S. Provisional Patent Application Ser. Nos. 60/463,930 and 60/464,003, both filed on Apr. 18, 2003, the entire contents of which are incorporated herein by reference.

TECHNICAL FIELD

The invention relates to new methods of making pro-urokinase mutants, e.g., for use in therapeutic lysis of occlusive blood clots.

BACKGROUND

The leading two causes of death listed by the World Health Organization (1998) are coronary heart disease and cerebrovascular disease. Since these diseases are largely triggered by occlusive blood clots, there is a considerable need for safe and effective thrombolytic agents (drugs capable of dissolving clots and restoring blood flow). However, blood clots also perform the essential physiological function of preventing hemorrhage by sealing injured vessels and tissues. This process is called hemostasis and most thrombolytic drugs interfere with hemostasis, and thereby induce bleeding at the sites of injured vessels and tissues.

When an intravascular clot or thrombus forms, blood flow is arrested at that site. Depending on the location in the arterial system, i.e., heart, brain, or leg, such an occlusive clot can trigger a heart attack, stroke, or peripheral gangrene. In the venous circulation the same process can cause thrombophlebitis (deep vein thrombosis) or pulmonary embolism (lung clots). Together, these cardiovascular diseases constitute the leading causes of death and disability in industrialized countries. Since the tendency to clot increases with age and populations are getting older, the incidence of those disorders is increasing worldwide.

As a result, there is a need for safe and effective thrombolytic agents. One such agent is pro-urokinase (pro-UK), a natural plasminogen activator that targets blood clots (see, e.g., Husain et al., U.S. Pat. No. 4,381,346). It is the proenzyme precursor of urokinase (UK). Pro-UK is better adapted to pharmacological use than UK, because it is inert in the blood (being a pro-enzyme) at physiological concentrations in the absence of a clot. Unfortunately, at therapeutic doses, which are significantly larger than naturally occurring concentrations, pro-UK becomes unstable and is readily converted to UK, which is a non-specific plasminogen activator with undesirable side effects.

Mutant forms of pro-UK are described in Liu et al., U.S. Pat. No. 5,472,692. These pro-UK mutants are said to have lower intrinsic activity than pro-UK, induce less fibrinogenolysis and non-specific plasminogen activation than pro-UK, and yet retain the same thrombolytic activity as pro-UK. In other words, the mutant pro-UKs have been described as performing in the same way as pro-UK, but with fewer side effects because they are more stable than pro-UK in blood at therapeutic concentrations.

SUMMARY

The invention is based, at least in part, on the discovery that a combination of specific process parameters can be used to prepare high yields of mutant forms of the pro-urokinase (pro-UK). These pro-UK mutants, such as pro-UK mutant "M5" (as defined herein), spare "good" fibrin clots (the hemostatic fibrin that seals injured blood vessels), while at the same time lysing the "bad" clots (that occlude blood vessels) when administered in therapeutic quantities, and at relatively fibrin-specific doses. The main parameters of the new methods are the use of a Phage T7 promoter, a Shine-Dalgarno sequence, and an $E.$ $coli$ type B strain BL21DE3 RIL as the host cell for the expression of a mutant human pro-UK gene that encodes these pro-UK mutants.

The present invention relates to recombinant DNA methods of producing non-glycosylated, single-chain mutants (e.g., $Lys^{300} \rightarrow His$) of pro-UK. More particularly, it relates to methods of producing non-glycosylated pro-UK mutants by modifying the nucleotide sequence that encodes native (wild-type) pro-UK, inserting the modified, e.g., mutagenized, nucleic acid sequence into a specific plasmid vector, introducing the resulting plasmid into a bacterial cell to produce a transformed cell, culturing the transformed cell, and recovering non-glycosylated pro-UK mutant proteins from the transformed bacterial cell.

In general, the invention features methods of preparing a pro-UK mutant polypeptide by (a) obtaining a nucleic acid molecule that encodes a pro-UK mutant polypeptide; (b) inserting the nucleic acid molecule into a pET29a expression plasmid comprising a phage T7 promoter and Shine-Dalgamo sequence; (c) transforming $E.$ $coli$ type B strain bacteria BL21/DE3 RIL with the expression plasmid; (d) culturing the transformed bacteria for a time and under conditions sufficient to enable the bacteria to express pro-UK mutant polypeptide; and (e) isolating the pro-UK mutant polypeptide from the transformed bacteria. Alternatively, one can obtain the required transformed bacteria, and follow the same culturing and isolation steps to obtain the pro-UK mutant polypeptide.

In these methods, the pro-UK mutant can be a pro-UK flexible loop mutant, e.g., M5. The pro-UK mutant can be non-glycosylated and has a molecular weight of about 45,000 daltons.

A pro-UK flexible loop mutant is a polypeptide that has the amino acid sequence of native (wild-type) pro-UK (which has 411 amino acids), but with one or more amino acids in the "flexible loop" (which includes the amino acids at locations 297–313) replaced by a neutral amino acid such as alanine (Ala) or an amino acid that can take on only a weak positive charge, such as histidine (His). These flexible loop mutants are described in U.S. Pat. No. 5,472,692. One example of a pro-UK flexible loop mutant is referred to herein as M5, which has the complete amino acid sequence of wild-type pro-UK, but with one amino acid alteration, $Lys^{300} \rightarrow His$.

In the new methods, the culturing can be a two-stage fermentation. For example, the first stage of fermentation can include adding to a flask a cell culture diluted in sterile EC1 medium and growing the culture at 34–37° C. overnight with agitation to form a seed culture, wherein the cell culture comprises a glycerol suspension of an LB culture of the transformed bacteria and containing a sufficient amount of kanamycin, e.g., 30 μg/ml. The second stage of fermentation can include a) adding the seed culture to a fermentor; b) maintaining the pH in the fermentor at about 6.5 to 7.5, e.g., 6.8; c) maintaining the dissolved oxygen concentration in the culture medium at 35–45%, e.g., 40%, of air saturation; d) maintaining the temperature of fermentation at about 34–37° C.; and e) adding to the fermentor a nutrient feeding solution, comprising one or more sugars, when all glucose initially present in the fermentor at step a) is consumed, following the equation $V=V_0\ e^{0.18t}$, where V=volume of feeding solution added (ml/h), Vo=1/100 of the starting fermentation medium (ml), and t=time of fermentation after the start of the feeding phase (hours). The plasmid can be pET29aUKM5, as described herein.

In some embodiments, the method can further include preparing a two-chain pro-UK mutant, e.g., two-chained M5 (tcM5), by passing the pro-UK mutant over plasmin bound to a substrate, e.g., an agarose-based gel filtration matrix such as Sepharose®.

In other aspects, the invention includes purified pro-UK mutant polypeptides, such as flexible loop mutants, e.g., M5 (both as described herein), produced according to the methods described herein. The isolated pro-UK mutant polypeptides have a purity of 96% or greater, i.e., they are in compositions in which at least 96, 97, 98, or even 99% of the protein in the composition is the single-chain pro-UK mutant polypeptide. The invention also features compositions including pro-UK mutants made according to the new methods and an excipient, e.g., an acidic excipient, as well as a composition including an aliquot of 20–40 mg of a pro-UK mutant made according to any the new methods, packaged with directions for use in administering as a bolus to a patient exhibiting symptoms of a stroke or a heart attack.

In another aspect, the invention also includes a purified culture of *E. coli* type B strain bacteria BL21DE3 RIL, wherein bacteria in the culture contain an expression plasmid encoding a pro-urokinase flexible loop mutant polypeptide, such as plasmid pET29aUKM5.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
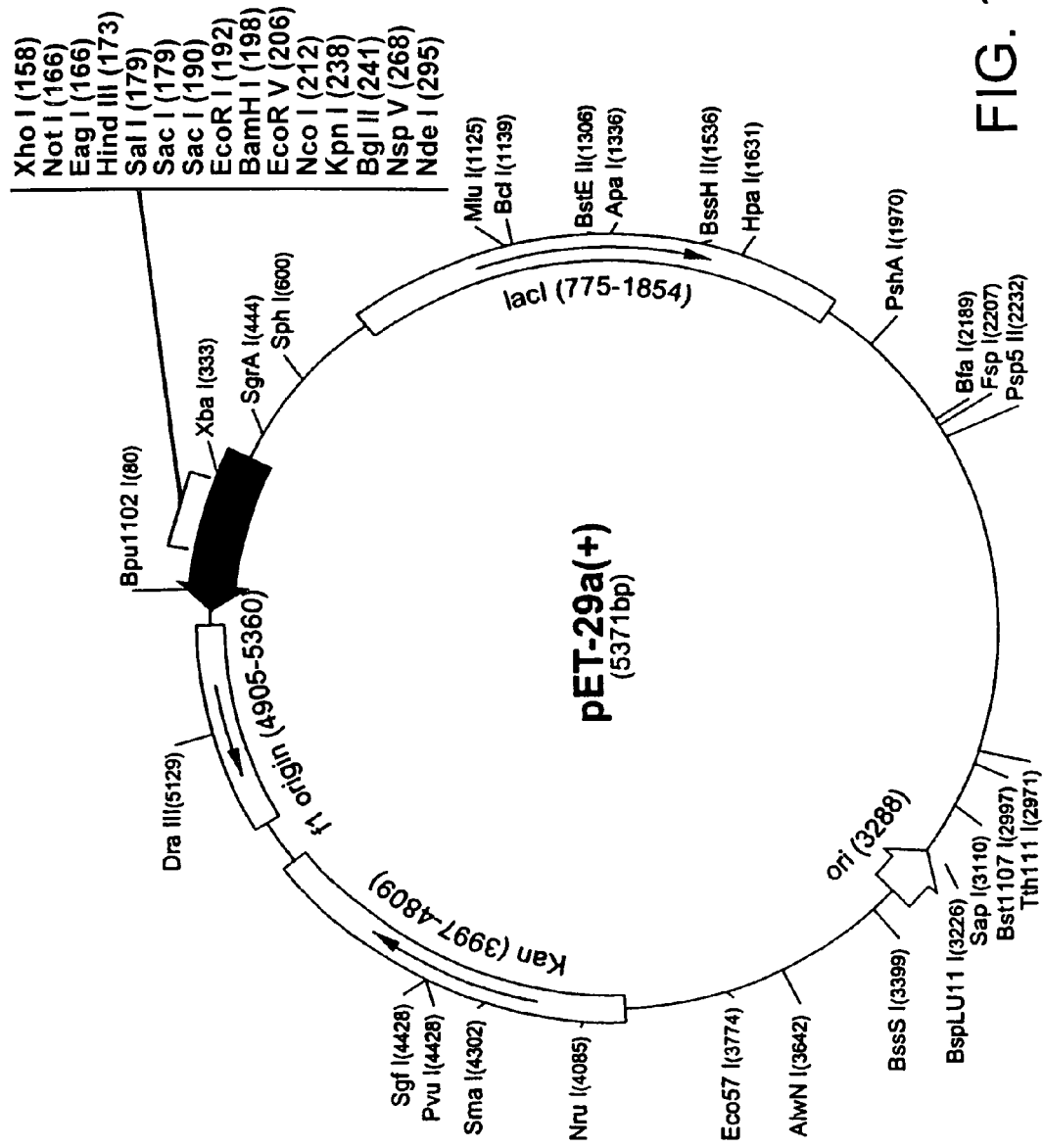
FIG. 1 is a representation of a plasmid (pET-29a) that is used in the new methods.

Certain mutant forms of pro-UK, so-called "pro-UK mutants," are faster than native pro-UK in lysing "bad," i.e., occlusive blood clots, and, in therapeutic quantity, are found to be relatively sparing of "good" or hemostatic (wound sealing) clots, so they cause little or no bleeding at tissue injuries, such as surgical sites. The bad clots are occlusive thrombi or emboli that include partially degraded fibrin, and the pro-UK mutants, such as pro-UK flexible loop mutants, are particularly effective against these types of clots. On the other hand, the hemostatic, wound sealing clots are comprised of intact fibrin, and the pro-UK flexible loop mutants spare these clots.

Based on these newly discovered characteristics, these pro-UK mutants can now be used for specific applications such as when a person suffers an apparent stroke or heart attack, or immediately before, during, or after surgery, e.g., where administration of thrombolytics currently has been too risky or even contraindicated. These effects and benefits of the pro-UK mutants are described in a co-pending application, "Methods, Devices, and Compositions for Lysis of Occlusive Blood Clots While Sparing Wound Sealing Clots," filed simultaneously herewith, on Apr. 16, 2004, which is incorporated herein by reference in its entirety.

Because of these unique characteristics and new methods of use, there is a need to produce pro-UK mutants, e.g., flexible loop mutants such as M5, in high quantities, at a high level of purity sufficient for administration to human patients, and with the proper protein refolding.

Methods of Making Pro-UK Mutants

Pro-UK mutants have the same amino acid sequence as native pro-UK but for a mutation, e.g., one or more point mutations, e.g., as described in U.S. Pat. No. 5,472,692. For example, pro-UK "flexible loop" mutants have one or more point mutations at one of the amino acids in the flexible loop (amino acid locations 297–313), e.g., at $Lys^{300}$, $Gly^{299}$, or $Glu^{301}$ with a simple, neutral amino acid such as alanine (Ala), glycine (Gly), and valine (Val), or a weakly positively charged amino acid such as histidine (His). Examples include $Lys^{300} \rightarrow His$ (referred to herein as the "M5" mutant), $Lys^{300} \rightarrow Ala$, $Gly^{299} \rightarrow His$, $Glu^{301} \rightarrow Ala$, $Gly^{299} \rightarrow Ala$, or $Glu^{301} \rightarrow His$ mutants. These pro-UK flexible loop mutants are described in U.S. Pat. No. 5,472,692, which is incorporated herein by reference in its entirety.

The pro-UK mutants must have the following characteristics: they must increase the stability of native pro-UK in plasma or blood by at least 3 times; they must enable administration in therapeutically effective dosages; and they must preferentially activate plasminogen in a third conformation found on degrading fibrin clots (occlusive clots) and spare plasminogen in its second (and first conformations) found on wound sealing clots (and floating freely in the blood). The pro-UK mutants can be flexible loop mutants, such as M5.

The pro-UK mutants are made, e.g., at a commercial scale, using the methods of production described herein. The goal in these methods is to obtain high expression and high yields of properly folded polypeptides from fermentation and purification procedures. These goals are achieved by careful selection of a combination of specific process parameters such as the type of bacterial strain, the particular expression plasmid, the specific promoter sequences, and the type of cell fermentation and protein purification techniques. By properly selecting these variables, recombinant bacteria are able to synthesize large amounts of the pro-UK mutant, e.g., flexible loop mutant, polypeptides, and it is possible to obtain the pro-UK mutants at high levels of purity. By employing these selected procedures, the properly folded pro-UK mutants, such as M5, can be produced at greater than 96, 97, 98, or even 99% of purity (i.e., they are in compositions in which at least 96 or greater percent of the protein in the composition is the single-chain pro-UK mutant polypeptide).

To isolate the desired recombinant *E. coli* strains, it is necessary to go through a number of steps including: (1)

mutagenizing the human pro-UK cDNA gene to isolate the desired M5 or other mutant gene; (2) inserting the mutated gene in an appropriate expression plasmid; (3) transforming a selected strain of E. coli with the engineered plasmid; (4) fermenting the transformed cells under appropriate conditions; and (5) isolating the pro-UK mutant protein. Each of these steps will be described in detail.

(1) Mutagenesis

The human pro-UK cDNA gene can be treated as described below to isolate the desired pro-UK mutant encoding gene. The general methods described in U.S. Pat. Nos. 5,866,358 and 5,472,692 can be applied to prepare the nucleic acid molecule encoding the particular desired pro-UK mutant polypeptide.

For example, the pro-UK mutants can be made using site-directed mutagenesis, such as oligonucleotide-directed mutagenesis, which allows the specific alteration of the existing native pro-UK nucleic acid sequence. The gene encoding native pro-UK is well characterized and is available, e.g., from Primm (Milano, Italy) or from the ATCC at Accession Nos. DNA 57329 or Bact/phage 57328. The sequence is also available from the NIH computer database Protein Identity Resource under the name UKHU. Production of a gene encoding M5 is described in U.S. Pat. No. 5,472,692.

In general, oligonucleotide-directed mutagenesis is accomplished by synthesizing an oligonucleotide primer whose sequence contains the mutation of interest, hybridizing the primer to a template containing the native sequence, and extending it, e.g., with T4 DNA polymerase. The resulting product is a heteroduplex molecule containing a mismatch due to the mutation in the oligonucleotide. The mutation is "fixed" upon repair of the mismatch in, e.g., E. coli cells. The details of this method are described, e.g., in Ausubel et al. (eds.), Current Protocols in Molecular Biology, Chapter 8.1 (Greene Publishing Associates 1989, Supp. 13). The details of this method are routine, and are described in U.S. Pat. No. 5,472,692.

Several variations of in vitro mutagenesis by primer extension that yield mutants with high efficiency have been developed, as described in Smith, Ann. Rev. Genet., 19:423–463 (1986), and various methods can be used to prepare the nucleic acid molecules encoding the pro-UK flexible loop mutants. One example of a simple site-directed mutagenesis protocol applied to a uracil-containing template, which allows rapid and efficient recovery of mutant DNAs, is described in Kunkel, Proc. Natl. Acad. Sci. U.S.A., 82:488–492 (1985), and Kunkel et al., Meth. Enzymol., 154:367–382 (1987).

(2) Insertion of Mutant Gene into Expression Vector

Once the pro-UK DNA with the desired mutation(s) is obtained, it must be cloned into a suitable expression vector. In particular, plasmid pET29a (kanamycin-resistant), which is shown in FIG. 1 can be used (available form Novagen). For example, pET29aUKM5 (which encodes the M5 pro-UK mutant) (FIG. 2) can be used as the expression vector to produce the specific pro-UK flexible loop mutant M5. In this plasmid, the gene encoding M5 is inserted into the Nde I-Sac I site (see FIG. 2) on the plasmid using standard techniques. The pET-29a plasmid includes specific Phage T7 promoter and Shine-Dalgamo sequences (see, e.g., (Moffatt and Studier, (1986) J. Mol. Biol., 189, 113–130; Rosenberg et al. (1987) Gene, 56, 125–135; and Studier et al., (1990) Meth. Ezymol., 185, 60–89)). The promoter is responsible for the synthesis of messenger RNA while the Shine-Dalgamo sequence should guarantee an efficient translation of the mRNA in the polypeptide chain.

Although this particular plasmid and sequences are known, and the techniques to combine these sequences and plasmids are also well known to those of ordinary skill in the field of molecular biology, the specific combination of these parameters has not been described prior to the present disclosure. The general techniques are described in detail, e.g., in Ausubel et al. (eds.), Current Protocols in Molecular Biology, Chapters 9 and 16, supra; and Sambrook, Fritsch, and Maniatis, Molecular Cloning (2d ed.), Chapter 16 (Cold Spring Harbor Laboratory Press, 1989).

(3) Transformation of the Plasmid into a Host Cell

Next, an E. coli type B strain, BL21DE3 RIL, is used for the expression and production of the pro-UK mutant. For example, insertion of plasmid pET29aUKM5 into E. coli type B strain BL21DE3 RIL (available, e.g., from STRATAGENE®, USA) induces very high levels of expression of the M5 polypeptide. Interestingly, insertion of the same plasmid into other strains of E. coli (type K-12, type C, or type W, and even other type B strains) does not provide as high a yield of M5.

For example, competent cells of strain BL21DE3 RIL can be prepared using a calcium chloride procedure of Mandel and Higa (Mol. Biol., 53:154, 1970). A small aliquot, e.g., 200 μl, of a preparation of these cells, e.g., at $1 \times 10^9$ cells per milliliter, can be transformed with plasmid DNA (approximate concentration from 2 to 10, e.g., 5 μg/ml). Transformants containing the kanamycin resistant plasmids are selected on plates of L-agar containing 30 μg/ml kanamycin.

One or more small colonies are streaked, e.g., with wooden toothpicks, onto L-agar containing the same antibiotic. After incubation at about 37° C., e.g., for a time sufficient to establish colonies, e.g., about 8, 10, 12, 15, or more hours, portions of the streaks can be tested for pro-UK mutant production by inoculation into LB medium (containing kanamycin at a concentration of 30 μg/ml, D-glucose at a concentration of 1 mg/ml, and Cloramphenicol at a concentration of 50 μg/ml) and incubated overnight, again at about 37° C. The following day, the cultures can be diluted, e.g., 1:100, in medium, such as LB medium, containing the same concentration of kanamycin, and incubated at 37° C. When the cell density of the cultures reach $O.D._{600}=0.6$ to 0.8 the cultures are induced with 1 mM IPTG for 4, 6, and 8 hours.

Total cell proteins from aliquots of culture medium ($O.D._{600}=1$ to 1.5) can be analyzed by sodium dodecylsulfate polyacrylamide gel electrophoresis (SDS-PAGE) as described in Laemmli, Nature, 227:680, 1970. A major protein band having a molecular weight corresponding to that of non-glycosylated M5 (45,000 daltons) should be observed for the samples.

Figure 4:
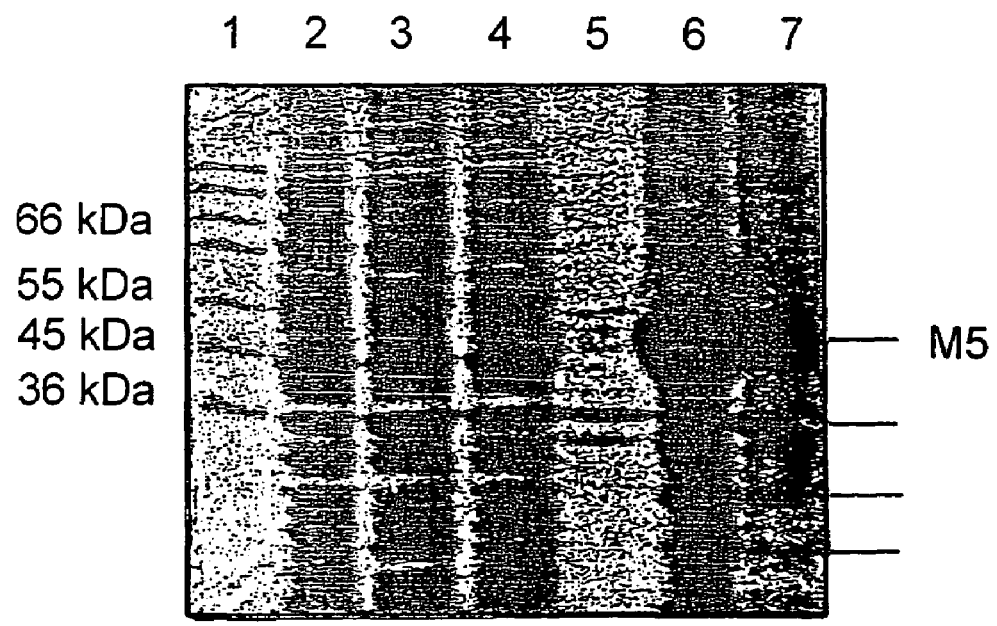
FIG. 4 is a representation of an electrophoresis gel showing the molecular weight of various proteins produced by various strains of *E. coli* and different plasmids.

FIG. 4 shows typical SDS-PAGE results. Lane 1 includes molecular weight standards. Lane 2 contains BL21(DE3) RIL[pET29a] supernatant of cells at an OD of 1.5. Lane 3 contains BL21(DE3)RIL[M5-PUK] supernatant of cells at an OD of 1.5. Lane 4 contains BL21(DE3) [M5-PUK] supernatant of cells at an OD of 1.5. Lane 5 contains BL21(DE3)RIL[pET29a] inclusion bodies of cells at an OD of 1.5. Lane 6 contains BL21 (DE3)RIL[M5-PUK] inclusion bodies of cells at an OD of 1.5. Lane 7 contains BL21(DE3) [M5-PUK] inclusion bodies of cells at an OD of 1.5. As explained in further detail in Example 1, below, these results indicate that M5 is an insoluble protein, and only the combination of the pET-29aUKM5 plasmid with BL21 (DE3)RIL produced large quantities of M5 (Lane 6).

Using the procedure described above, several additional E. coli host strains were screened with the objective to isolate a transformant strain able to produce M5 at high levels. Plasmid pET29aUKM5 was transformed into the following strains: BL21DE3, BL21DE3 pLys, JM109/DE3, and HB 101/DE3. None of these transformed strains was able to yield high quantities of the M5 polypeptide as seen with the host strain BL21DE3 RIL, indicating that indeed the combination of the specific expression plasmid with strain BL21DE3 RIL is an important combination to obtain high quantities of M5. The details of these tests are described in Example 2, below.

We note that the use of B strains according to the present invention yields cell extracts with low proteolytic activity, i.e., low contamination with UK.

(4) Fermentation of the Host Cells

The transformed bacterial cells must then be cultured at high biomass in appropriate fermentors. The protocol developed and used for the production of pro-UK flexible loop mutants is based on the following two stages of fermentation.

A. First Fermentation Stage (Seed Culture)

The first fermentation phase is carried out in flasks to obtain a seed culture large enough to inoculate the production stage (second fermentation stage). One vial of "working cell bank" (e.g., 0.1 ml–1.0 ml) is diluted in an amount (e.g., 50 to 500 ml, e.g., 100 ml) of sterile medium (e.g., EC-1 medium, details of which are provided in Table 1 in Example 3, below) and growth at about 37° C. overnight with the agitation.

The working cell bank is made of a glycerol suspension of an overnight culture (e.g., LB medium) of the pro-UK flexible loop mutant producing strain (e.g., BL21DE3 RIL carrying plasmid pET29aUKM5 that encodes M5), and containing an antibiotic to select for bacteria carrying a resistant plasmid (e.g., kanamycin at 30 μg/ml, chloramphenicol at 30 μg/ml, and 0.1% w/v D-Glucose).

B. Second Fermentation Stage

The second stage includes the following steps:
1) the seed culture, prepared in a flask, is added to a fermentor (e.g., a 1:100 dilution in EC-1 medium; e.g., 20 ml into 2.0 liters or 100 ml into 10 liters);
2) the pH in the fermentor is kept at about 6.8 to 7.2, e.g., 7.0, for example, by using a solution of 28% (v/v) ammonia water;
3) dissolved oxygen is maintained at about 35 to 45%, e.g., about 38, 40, or 42%, of air saturation by increasing the agitation speed and by changing the percentage of pure oxygen;
4) the temperature of fermentation is kept at about 34–37° C.; and
5) a nutrient feeding solution that contains one or more sugars (e.g., glucose) and other nutrients (for a specific example, see Table 2 in Example 3, below) is added exponentially when all the glucose initially present is consumed (usually after 8 hours), following the equation $V=V_0 e^{0.18t}$, where V=volume of feeding solution added (ml/h), $V_0=\frac{1}{100}$ of the starting fermentation medium (ml), and t=time of fermentation after the start of the feeding phase (hours).

In this method, gene expression is induced by adding IPTG, e.g., at a final concentration of 1.2 mM, when the fermentation reaches a cell density of about 90 $OD_{600}$.

The post-induction fermentation is generally prolonged for 6 hours to allow the cells to produce the pro-UK mutant. Samples of 0.5 ml are removed from the fermentor every 2 hours for analysis.

(5) Isolating and Purifying Pro-UK Mutants

After the mutant pro-UK is expressed by a bacterial cell line, it must be extracted from the cells and purified. Purification of active mutant pro-UK from culture medium or cell extracts generally involves the steps of:
1) pellet recovery,
2) protein refolding,
3) concentration by ultrafiltration,
4) cation exchange chromatography,
5) anion exchange chromatography,
6) hydroxyapatite chromatography,
7) gel filtration chromatography
8) buffer exchange, and
9) freeze drying.

These steps are described in further detail as follows.

1. Pellet Recovery

In specific embodiments, the broth from a 2-liter fermentation is collected at about 4° C. at 9950×g for 15 minutes using, e.g., a Beckman J2-MI centrifuge. Other methods can be used to create a pellet. The cellular pellet is resuspended at 4° C. in 1.1 liters of a buffer comprising 0.025 M monobasic sodium phosphate, 0.125 M sodium chloride, pH 7.5 containing 0.1% Triton×100. This slurry is passed through a French-Pressure-Cell 20K (Aminco) at 1000 psi. The temperature is controlled during this operation to about 5–10° C. After each passage through the French pressure cell, the cell suspension is sonicated at 15 mV for about 1 minute, e.g., using a Microson™ Ultrasonic cell disruptor XL (Misonix).

Six passes under these conditions are made to achieve greater than 90% cell breakage (controlled by microscopic observation). A further passage may be made if necessary. Other methods can be used to achieve 90% cell breakage.

The resulting cell lysate is centrifuged at 4° C. at 9950×g for 15 minutes using, for example, a Beckman J2-MI centrifuge. The solid is resuspended in 1 liter of buffer: 0.025 M monobasic sodium phosphate, 0.125 M sodium chloride, pH 7.5 containing 0.1% Triton×100. The slurry is passed again twice through the French press under the conditions described above, and centrifuged at about 4° C. at 9950×g for 15 minutes using the centrifuge.

The slurry resulting from this process is the starting material for the activation and purification process and is divided into suitable aliquots. Other methods can be used to obtain a similar cell lysate slurry.

2. Refolding

In specific embodiments, a quantity of the material coming from the slurry obtained, as described above, corresponding to about 6 g of protein (judged by Lowry or Biuret protein assay) is dissolved in a 1.2 liters of 6 M guanidine HCl, 0.01 M TRIS, pH 8.5, L-cysteine 0.1 M, for at least 10 hours at 4–6° C. The solution is centrifuged at 4° C. at 9950×g for 15 minutes using a centrifuge, and then diluted with 30 liters of a buffer comprising 2.5 M Urea, 0.01 M TRIS, 0.005 M EDTA (pH 8). The solution is stirred gently at 14–16° C. for at least 18 hours. During this period the active product is formed from the previously inactive protein. Other standard methods of protein refolding can be used.

3. Concentration

The solution obtained from the refolding process (2) is pre-filtered, e.g., using an Opticap® 10" cartridge (Millipore), and then concentrated, e.g., about 25 times from its initial volume, using an ultrafiltration system (e.g., a Millipore ProFlux® M12 with Pellicon® 2 cartridges, 10,000 M.W.t. cut off). The concentrated material can then be diafiltrated against two volumes of a buffer consisting of 2.5 M Urea, 0.01 M TRIS, 0.005 M EDTA, pH 7.6.

4. Cation Exchange Chromatography

The solution obtained from the concentration step (3) is centrifuged at 4° C. at 9950×g for 15 minutes using a Beckman J2-MI centrifuge, and then applied to a cation exchange column, e.g., a HiPrep™ 16/10 SP FF (Amersham Biosciences), previously equilibrated with the same dilution buffer. After loading, the column is washed with two column volumes of the equilibrating buffer followed by four column volumes of 0.01 M TRIS (ph 7.6) buffer. The column is then eluted in fractions with 0.01 M TRIS, 0.5 M sodium chloride, pH 7.6 buffer.

5. Anion Exchange Chromatography

The pool fractions from cation exchange chromatography are loaded onto an anion exchange column, e.g., a HiPrep 16/10 Q FF (Amersham Biosciences), previously equilibrated with 0.01 M TRIS, 0.5 M sodium chloride, pH 7.6 buffer. The column flow-through containing the product is collected. After loading, the column is washed using 2–3 column volumes of the equilibrating buffer.

The combined load flow-through and column wash solutions form the input for the next chromatographic column.

6. Hydroxyapatite Chromatography

The material obtained from the anion exchange column is applied to a column of hydroxyapatite, such as a High Resolution (Calbiochem) column, previously equilibrated in 0.01 M TRIS, 0.5 M sodium chloride, pH 7.6 buffer. After loading, the column is washed with 2 column volumes of the equilibrating buffer, followed by 1 column volume of 1 mM sodium phosphate, 0.5 M sodium chloride, pH 7.6 buffer.

The column is eluted in fractions with 20 mM sodium phosphate, 0.5 M sodium chloride, pH 7.6 buffer. A pool of these fractions is made on the basis of the quantity and purity judged by the specific activity. Depending on the pool volume, the resulting material may be concentrated by ultrafiltration (e.g., using a Pellicon 2 cartridge, 10,000 M.W.t. cut off) to a suitable volume for the following step.

7. Gel Filtration Chromatography

The material resulting from the hydroxyapatite chromatography is loaded directly (or after concentration) on to a column of HiLoad 26/60 Superdex® 75 (Amersham Biosciences), previously equilibrated in 0.01 M TRIS, 0.5 M sodium chloride, 0.005 M EDTA, pH 8. The column is eluted in fractions using the equilibration buffer.

Pool fractions are selected on the basis of specific activity, SDS PAGE (reduced and non reduced) and HPLC purity.

8. Buffer Exchange

The resulting material, pooled from gel filtration chromatography, is applied to column of HiPrep 26/10 desalting (Amersham Biosciences), previously equilibrated in 0.05 M ammonium bicarbonate buffer. The column is eluted in fractions with this buffer. A pool of fractions is prepared on the basis of OD 280 nm and conductivity.

9. Freeze Drying

The solution resulting from the buffer exchange stage is divided into aliquots, e.g., of 10 mg in vials of 100 ml, and then frozen, e.g., for 2 hours at −80° C. The frozen material is then lyophilized, e.g., using a CT 60e (Heto) freeze-drier for 72 hours.

Alternative methods of protein isolation and purification can be used and are well known to those of ordinary skill in the field of molecular biology. Various protocols are described in Current Protocols in Molecular Biology, Chapter 10.

The new methods described herein can also be used to produce various biologically active fragments of the pro-UK flexible loop mutants. For example, one set of active fragments is known as low molecular weight ("LMW") pro-UK flexible loop mutants. These mutants have the same sequence as the full-length pro-UK mutants, but are cleaved at the Lys$^{135}$ amino acid location of the molecule, e.g., with plasmin or trypsin, to form a smaller size (33K vs. 50K) protein molecule. These LMW pro-UK mutants have improved diffusion characteristics because of their smaller size. These LMW pro-UK mutants can also be activated to produce LMW two-chain mutant UK, e.g., by passing the single-chain form over a column of Sepharoseg®-bound plasmin.

One can also produce activated pro-UK flexible loop mutants (mutant UK) by passing the pro-UK mutants over plasmin bound to Sepharose®, e.g., in columns or in batch methods.

Storing and Administering Pro-UK Mutants

Once the pro-UK mutants are made, they can be lyophilized or stored in physiologically acceptable excipients, such as organic acids, e.g., acetic acid at a pH of about 5.4. The pro-UK mutants are quite stable in such acids, and can actually be stored over time and then administered directly to patients in such an acid solution. The pro-UK mutant proteins can also be combined with other drugs to form compositions that can then be administered to a patient in one solution.

In general, bolus or "loading" doses of the pro-UK mutants will be in the 20–40 mg range. The intravenous infusion dose of pro-UK flexible loop mutants such as M5 is about 120–200 mg/hour (e.g., 100, 125, 150, or 175 mg/hour), whereas the intra-arterial infusion rate will be 50–100 mg/hour (e.g., 60, 70, 80, or 90/mg/hour). Intra-arterial administration of pro-UK mutants will also provide additional efficacy and safety in the treatment of stroke patients.

The pro-UK in lyophilized form can be administered with a device that contains the pro-UK powder in one compartment, and in a second compartment contains a pre-measured amount of an excipient, such as sterile saline, purified water, or some other physiologically acceptable carrier in which the pro-UK powder can be reconstituted. The first and second compartments are connected by a wall such that the wall can be broken by the user of the device just prior to injecting the pro-UK solution. Thus, the device can be stored for long periods of time, and then the pro-UK powder can be reconstituted as required without the need to measure the amount of the excipient.

In addition, the pro-UK can be packaged in, specific aliquots and at specific concentrations, e.g., in predetermined dosages ready for administration, along with instructions to administer the pro-UK mutant, such as a flexible loop mutant, e.g., M5, to a person exhibiting symptoms of stroke or symptoms of a heart attack. For example, a plastic IV bag containing M5 for infusion can be labeled for use post-operatively, after angioplasty, or upon observing symptoms of a heart attack or stroke. In addition, a syringe for administering a bolus injection of M5, e.g., for use by an EMT in an ambulance, can be pre-loaded with a bolus of 20, 25, 30, 35, or 40 mg of a pro-UK mutant, such as M5, and labeled for immediate use on a person exhibiting symptoms of an apparent stroke or a heart attack.

EXAMPLES

The invention is further described in the following examples, which do not limit the scope of the invention described in the claims.

Example 1

Preparation of M5

Competent cells of strain BL21DE3 RIL were prepared using a calcium chloride procedure of Mandel and Higa (Mol. Biol., 53:154, 1970). 200 µl of a preparation of these cells at $1\times10^9$ cells per milliliter was transformed with 2 µl of plasmid pET29aUKM5 that encodes M5 (approximate concentration 5 µg/ml). Transformants were selected on plates of L-agar containing 30 µg/ml kanamycin.

Figure 2:
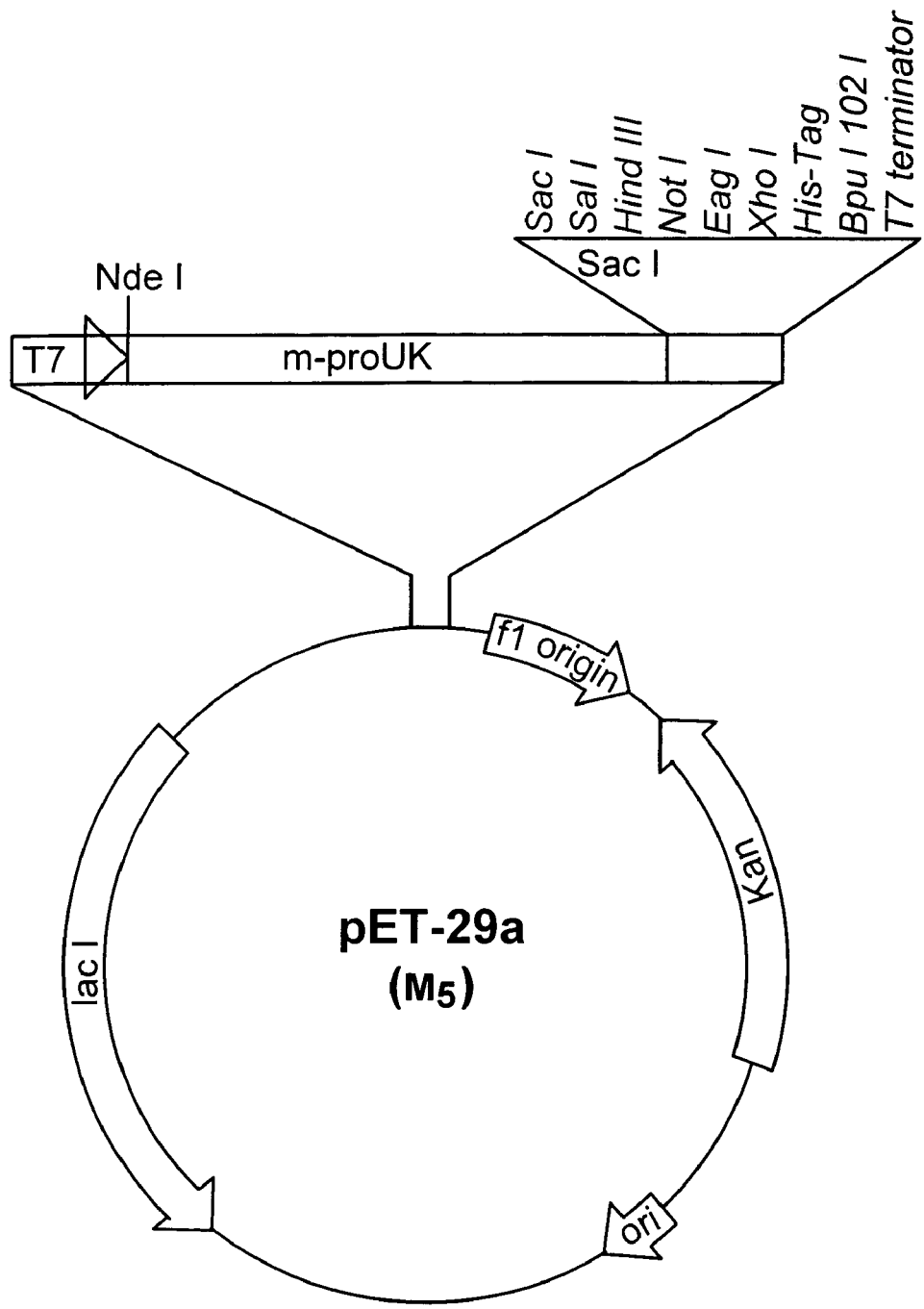
FIG. 2 is a representation of the pET-29aUKM5 plasmid.
Figure 3:
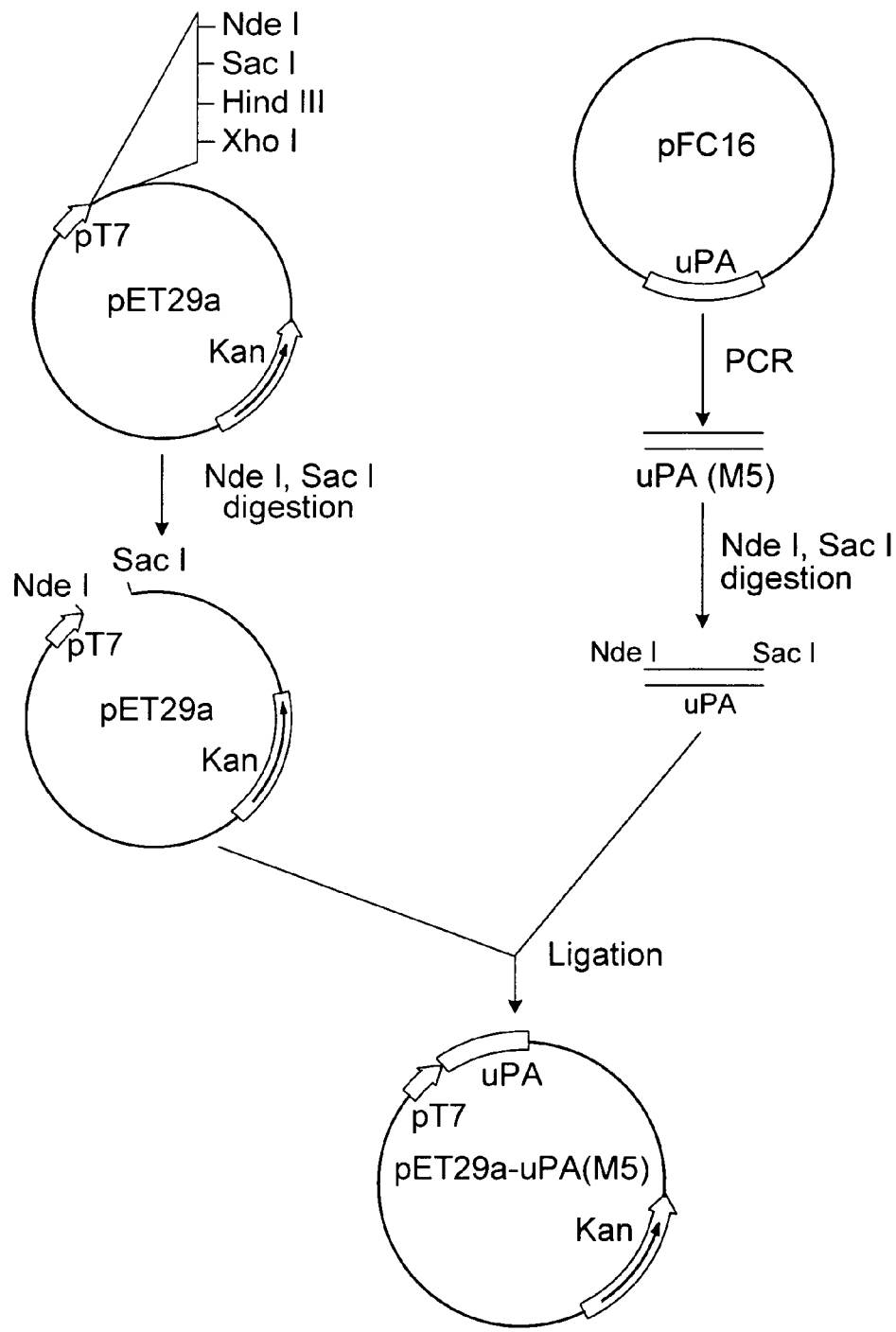
FIG. 3 is a representation of a method to construct the pET-29aUKM5 plasmid.

Plasmid pET29aUKM5 was made starting with plasmid pET29a (Novagen) shown in FIG. 1. As shown in FIGS. 2 and 3, to construct pET29-u-UKM5 for the expression of pro-UK (M5), the pro-UK (M5) gene was amplified from plasmid pFC16 by the polymerase chain reaction using the following primers:

```
Primer 1 (5' GAG GAT TAC ATA TGA GCA ATG AGC 3'),           (SEQ ID NO: 1)

Primer 2 (5' CTG GGG ACC GAG CTC TCA GAG, GGC CAG GCC ATT 3') (SEQ ID NO: 2)

Primer 3 (5' GGC TTT GGA CAC GAG AAT TCT ACC GAC TAT CTC 3'). (SEQ ID NO: 3)
and Primer 4 (5' AGA ATT CTC GTG TCC AAA GCC AGT GAT CTC AC 3'). (SEQ ID NO: 4)
```

Primer 3 and Primer 4 were used to mutate $Lys^{300} \rightarrow His$. Primer 1 and Primer 2 were used to incorporate NdeI and SacI restriction sites immediately 5' to the first codon and immediately 3' to the stop codon of pro-UK M5 cDNA, respectively. The amplified pro-UK M5 (M5) gene was digested with NdeI and SacI, purified, and ligated with the large fragment of NdeI-SacI-digested pET29a. The sequence of the pro-UK M5 (M5) coding region was confirmed by DNA sequencing.

Two small colonies were streaked with wooden toothpicks (each as three streaks about 1 cm long) onto L-agar containing the same antibiotic. After 12 hours of incubation at 37° C., portions of the streaks were tested for M5 production by inoculation onto 10 ml of LB medium (containing kanamycin at a concentration of 30 µg/ml, D-glucose at a concentration of 1 mg/ml, and cloramphenicol at a concentration of 50 µg/ml) and incubated overnight at 37° C. The following day, the cultures were diluted 1:100 in M9 medium, containing the same concentration of kanamycin, and incubated for 6 hours at 37° C. When the cell density of the cultures reached $O.D._{600}=0.6$ to 0.8, the cultures are induced with 1 mM IPTG for 4, 6, and 8 hours.

Total cell proteins from 250 µl aliquots of culture ($O.D._{600}=1$ to 1.5) were analyzed by sodium dodecylsulfate polyacrylamide gel electrophoresis (SDS-PAGE) as described in Laemmli, Nature, 227:680, 1970. A major protein band having a molecular weight corresponding to that of non-glycosylated M5 (45,000 daltons) was observed for the two independent samples.

FIG. 4 shows the SDS-PAGE results. Lane 1 includes molecular weight standards. Lanes 2, 3, and 4 show the results of the supernatants at an OD of 1.5. Since M5 is an insoluble protein, we did not expect to find M5 in the supernatant, and found none. The band at about 45 kDa is a soluble host protein. Lane 2 contains BL21(DE3)RIL [pET29a], which lacks the M5 encoding gene. Lane 3 contains BL21(DE3)RIL[M5-PUK], which has the M5 encoding gene, and the RIL strain, but since M5 is insoluble, we found none in this lane. Lane 4 BL21(DE3) [M5-PUK], which has the M5 encoding gene, but not the RIL strain. Again, there was no M5 in the supernatant.

Lanes 5, 6, and 7 show the results of the pellet ("inclusion bodies"), again at an OD of 1.5. Lane 5 contains BL21(DE3) RIL[pET29a] (no M5 encoding gene), and as expected, it shows no M5. Lane 6 contains BL21(DE3)RIL[M5-PUK], which has the M5 encoding gene, and the RIL strain, and shows a very high level of M5. Lane 7 contains BL21(DE3) [M5-PUK], which has the M5 encoding gene, but not the RIL strain. This strain does produce some M5, but not nearly as much as the RIL strain.

A set of streaks corresponding to colony no. 2 (clone 2) was chosen arbitrarily for further characterization and then selected as an M5 producing strain.

Example 2

Testing of Alternate Host Cells

Using the procedure described herein and in Example 1, several additional *E. coli* host strains were screened with the objective to isolate a transformant strain able to produce M5 at high levels. Plasmid pET29aUKM5 was introduced into the following strains: BL21DE3, BL21DE3 pLys, JM109/DE3, and HB 101/DE3. None of these strains, when transformed with plasmid pET29aUKM5, was able to yield high quantities of the M5 polypeptide as seen with the host strain BL21DE3 RIL, indicating that the combination of the specific expression plasmid with strain BL21DE3 RIL is an important combination to obtain high quantities of M5. For example, the following yields were obtained:

| Host strain | Productivity |
| --- | --- |
| BL21(DE3) RIL | 4.12 grams/liter |
| BL21(DE3) | 0.91 grams/liter |
| BL21(DE3)pLys | 0.82 grams/liter |

The productivity is expressed as quantity of M5 polypeptide as measured by SDS PAGE analysis and quantified against a standard of pro-UK. Thus, it is clear that the combination of the specific plasmid and its Phage T7 promoter sequences and strain BL21DE3/RIL provides a far greater yield than even other type B strains. This data quantifies the results seen in Lanes 6 and 7 of FIG. 4. Although the *E. coli* type B strain BL21 (DE3) produces some M5, the BL21(DE3)RIL strain produces about 4.5 times as much M5.

Example 3

Fermentation of the Host Cells

Transformed bacterial cells are cultured at high biomass in appropriate fermentors as follows. A first fermentation phase was carried out in Erlenmeyer flasks to obtain a seed culture large enough to inoculate the production stage (second fermentation stage). One vial of working cell bank (0.1 ml) was diluted in 100 ml of sterile EC1 medium (details are provided in Table 1 below) and grown at 37° C. overnight with the agitation of 220 rpm.

The working cell bank was made of a glycerol suspension of an overnight LB culture containing kanamycin at 30 μg/ml and chloramphenicol at 30 μg/ml of the M5 producing strain (BL21/DE3 RIL carrying plasmid pET29aUKM5).

TABLE 1

Medium EC-1

| | Per liter: | Glucose | 10 g |
|---|---|---|---|
| | | Yeast extract | 1 g |
| | | $(NH_4)_2HPO_4$ | 2 g |
| | | $K_2HPO_4$ | 6.75 g |
| | | $MgSO_4 \times 7H_2O$ | 0.7 g |
| | | Citric acid | 0.85 g |
| | | TMS (see below) | 5 ml |
| TMS: Per liter | | $FeSO_4 \times 7 H_2O$ | 10 g |
| of 5 M HCl | | $ZnSO_4 \times 7 H_2O$ | 2.25 g |
| | | $CaCl_2 \times 2 H_2O$ | 2 g |
| | | $CuSO_4 \times 5 H_2O$ | 1 g |
| | | $MnSO_4 \times 5 H_2O$ | 0.23 g |
| | | $Na_2B_4O_7 \times 10 H_2O$ | 0.23 g |
| | | $(NH_4)_6MO_7O_{24}$ | 0.1 g |

A second fermentation stage includes the following steps:

(1) 20 ml of the seed culture, prepared in the Erlenmeyer flask, was added to 2.0 liters of EC-1 medium in a fermentor;

(2) the pH in the fermentor was kept at 6.8 using a solution of 28% (v/v) ammonia water;

(3) D.O. was maintained at 40% of air saturation by increasing the agitation speed and by changing the percentage of pure oxygen;

(4) the temperature of fermentation was kept at 35° C.; and (5) a nutrient feeding solution (described in further detail in Table 2 below) was added exponentially when all the glucose initially present is consumed (usually after 8 hours), following the equation $V=Vo \ e^{0.18t}$, where V=volume of feeding solution added (ml/h), Vo=1/100 of the starting fermentation medium (ml), and t=time of fermentation after the start of the feeding phase (hours).

TABLE 2

Feeding Solution

| Per liter: | Glucose | 400 g |
|---|---|---|
| | Yeast extract | 100 g |

In this method, gene expression was induced by adding IPTG at a final concentration of 1.2 mM, when the fermentation reached a cell density of 90 $OD_{600}$.

The post-induction fermentation was prolonged for 6 hours to allow the cells to produce M5. Samples of 0.5 ml were removed every 2 hours for analysis.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a pro-urokinase ("pro-UK") mutant polypeptide, the method comprising
   (a) obtaining a nucleic acid molecule that encodes a pro-UK mutant polypeptide;
   (b) inserting the nucleic acid molecule into a pET29a expression plasmid comprising a phage T7 promoter and Shine-Dalgarno sequence;
   (c) transforming *E. coli* type B strain bacteria BL21/DE3 RIL with the expression plasmid;
   (d) culturing the transformed bacteria for a time and under conditions sufficient to enable the bacteria to express pro-UK mutant polypeptide; and
   (e) isolating the pro-UK mutant polypeptide from the transformed bacteria.

2. The method of claim 1, wherein the pro-UK mutant is a pro-UK flexible loop mutant.

3. The method of claim 2, wherein the pro-UK flexible loop mutant comprises the mutation $Lys^{300} \rightarrow His$.

4. The method of claim 1, wherein the pro-UK mutant is non-glycosylated and has a molecular weight of about 45,000 daltons.

5. The method of claim 1, wherein culturing comprises a two-stage fermentation.

6. The method of claim 5, wherein the first stage of fermentation comprises adding to a flask a cell culture diluted in sterile EC1 medium and growing the culture at about 34 to 37° C. for at least about 10 hours with agitation to form a seed culture, wherein the cell culture comprises a glycerol suspension of an LB culture of the transformed bacteria and containing a sufficient amount of kanamycin to provide selection for kanamycin resistance.

7. The method of claim 5, wherein the second stage of fermentation comprises
   a) adding the seed culture to a fermentor;
   b) maintaining the pH in the fermentor at about 6.8 to 7.2;
   c) maintaining the dissolved oxygen concentration in the culture medium at about 35 to 45% of air saturation;
   d) maintaining the temperature of fermentation at about 34 to 37° C.; and
   e) adding to the fermentor a nutrient feeding solution comprising one or more sugars when all glucose initially present in the fermentor at step a) is consumed, following the equation $V = V_o \, e^{0.18t}$, where V=volume of feeding solution added (ml/h), $V_o = \frac{1}{100}$ of the starting fermentation medium (ml), and t=time of fermentation after the start of the feeding phase (hours).

8. The method of claim 1, wherein the expression plasmid containing the nucleic acid molecule is pET29aUKM5.

9. The method of claim 1, further comprising preparing two-chain pro-UK mutant by passing the pro-UK mutant over plasmin bound to a substrate.

10. The method of claim 9, wherein the substrate is an agarose-based gel filtration medium.

11. The method of claim 1, further comprising combining the isolated pro-UK mutant polypeptide with an acidic excipient.

12. A composition comprising an isolated, single-chain pro-urokinase ("pro-UK") mutant polypeptide produced according to the method of claim 1, wherein at least 96% of the protein in the composition is the single-chain pro-UK mutant polypeptide.

13. A composition of claim 12, wherein at least 98% of the protein in the composition is the pro-UK mutant polypeptide.

14. The composition of claim 12, wherein the pro-UK mutant polypeptide is a pro-UK flexible loop mutant.

15. The polypeptide of claim 12, wherein the pro-UK mutant is M5.

16. The composition of claim 12, further comprising a pharmaceutically acceptable excipient.

17. A composition of claim 16, wherein the pharmaceutically acceptable excipient is an acidic excipient.

18. A composition comprising an aliquot of 20 to 40 mg of a pro-UK mutant made by the method of claim 1, packaged with directions for use in administering as a bolus to a patient exhibiting symptoms of a stroke or a heart attack.

19. A purified culture of *E. coli* type B strain bacteria BL21DE3 RIL, wherein bacteria in the culture comprise an expression plasmid encoding a pro-urokinase flexible loop mutant polypeptide.

20. The culture of claim 19, wherein the expression plasmid is pET29aUKM5.

21. A method of preparing a pro-urokinase ("pro-UK") mutant polypeptide, the method comprising
   (a) obtaining a transformed bacteria, wherein the bacteria is an *E. coli* type B strain bacteria BL21DE3 RIL transformed with a pET29a expression plasmid comprising a phage T7 promoter, a Shine-Dalgamo sequence, and a nucleic acid molecule that encodes a pro-UK mutant polypeptide;
   (b) culturing the transformed bacteria for a time and under conditions sufficient to enable the bacteria to express pro-UK mutant polypeptide; and
   (c) isolating the pro-UK mutant polypeptide from the transformed bacteria.

22. The method of claim 21, wherein the pro-UK mutant is a pro-UK flexible loop mutant.

23. The method of claim 22, wherein the pro-UK flexible loop mutant comprises the mutation $Lys^{300} \rightarrow His$.

24. The method of claim 21, wherein the expression plasmid containing the nucleic acid molecule is pET29aUKM5.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaggattaca tatgagcaat gagc                                            24

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctggggaccg agctctcaga gggccaggcc att                                  33

<210> SEQ ID NO 3
<211> LENGTH: 33
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 3
ggctttggac acgagaattc taccgactat ctc                                    33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agaattctcg tgtccaaagc cagtgatctc ac                                     32
```